(12) United States Patent
Van Den Houdt et al.

(10) Patent No.: US 9,532,852 B2
(45) Date of Patent: Jan. 3, 2017

(54) HEATING APPARATUS FOR MATERIALS USED IN DENTAL TREATMENT

(75) Inventors: Andreas Adrianus Lambertus Van Den Houdt, Breda (NL); Franciscus Maria Verhoeven, Amsterdam (NL)

(73) Assignee: NYAMBE B.V., Breda (NL)

( * ) Notice: Subject to any disclaimer, the term of this patent is extended or adjusted under 35 U.S.C. 154(b) by 130 days.

(21) Appl. No.: 14/241,145

(22) PCT Filed: Aug. 30, 2012

(86) PCT No.: PCT/EP2012/066865
§ 371 (c)(1),
(2), (4) Date: Feb. 26, 2014

(87) PCT Pub. No.: WO2013/030279
PCT Pub. Date: Mar. 7, 2013

(65) Prior Publication Data
US 2014/0212829 A1    Jul. 31, 2014

(30) Foreign Application Priority Data

Sep. 1, 2011    (NL) .................................... 2007327

(51) Int. Cl.
*F24H 7/00*    (2006.01)
*F27D 11/00*   (2006.01)
*A61C 5/04*    (2006.01)

(52) U.S. Cl.
CPC *A61C 5/045* (2013.01); *A61C 5/04* (2013.01)

(58) Field of Classification Search
None
See application file for complete search history.

(56) References Cited

U.S. PATENT DOCUMENTS

| | | | | |
|---|---|---|---|---|
| 1,865,472 A | * | 7/1932 | Lamstein | B01L 7/00 219/385 |
| 2,282,070 A | * | 5/1942 | Mahannah | B01L 7/00 219/405 |
| 2,836,696 A | * | 5/1958 | Ratchford | B29B 13/023 126/19 R |
| 3,607,134 A | * | 9/1971 | McIntyre | B01L 7/04 206/216 |
| 3,902,043 A | * | 8/1975 | Rogan | A61C 13/20 219/230 |

(Continued)

FOREIGN PATENT DOCUMENTS

| | | |
|---|---|---|
| DE | 44 02 238 | 7/1995 |
| FR | 2 797 174 | 2/2001 |

OTHER PUBLICATIONS

International Search Report for PCT/EP2012/066865, mailed Oct. 8, 2012.
Written Opinion for PCT/EP2012/066865, mailed Oct. 8, 2012.

*Primary Examiner* — Thor Campbell
(74) *Attorney, Agent, or Firm* — Nixon & Vanderhye P.C.

(57) ABSTRACT

A heating apparatus (10) for heating materials used in dental treatment is provided. The heating apparatus (10) comprises a heating compartment (33) with a heating element (35) for heating air inside the heating compartment (33), at least one socket for receiving and holding at least a part of the materials used in dental treatment inside the heating compartment (33), and an airflow generator (32, 34) for generating an airflow in the heating compartment (33).

13 Claims, 5 Drawing Sheets

(56) References Cited

U.S. PATENT DOCUMENTS

| | | | | |
|---|---|---|---|---|
| 3,932,114 A * | 1/1976 | Ebert | B29D 12/02 | |
| | | | 34/267 | |
| 4,054,376 A * | 10/1977 | Wareham | G02C 13/00 | |
| | | | 165/104.16 | |
| 4,132,216 A * | 1/1979 | Guibert | F25D 25/00 | |
| | | | 126/21 A | |
| 4,256,697 A * | 3/1981 | Baldwin | B01L 7/02 | |
| | | | 219/433 | |
| 4,270,892 A * | 6/1981 | Faunce | A61C 5/00 | |
| | | | 264/16 | |
| 4,349,725 A * | 9/1982 | Sheridan | A61C 17/022 | |
| | | | 392/383 | |
| 4,625,867 A * | 12/1986 | Guibert | F24C 15/322 | |
| | | | 126/21 A | |
| 4,865,864 A * | 9/1989 | Rijswijck | A23L 1/0135 | |
| | | | 219/400 | |
| 4,876,436 A * | 10/1989 | Ide | F24H 3/0411 | |
| | | | 219/505 | |
| 5,215,461 A * | 6/1993 | Riazi | A61C 5/04 | |
| | | | 433/102 | |
| 5,248,870 A * | 9/1993 | Redal | H05B 3/009 | |
| | | | 211/74 | |
| 5,266,777 A * | 11/1993 | Oppawsky | A61C 13/20 | |
| | | | 219/390 | |
| 5,286,423 A * | 2/1994 | Johnson | A61O 5/04 | |
| | | | 264/16 | |
| 5,372,759 A * | 12/1994 | Johnson | A61O 5/04 | |
| | | | 264/16 | |
| 5,410,130 A * | 4/1995 | Braunstein | B01L 7/52 | |
| | | | 219/386 | |
| 5,578,230 A * | 11/1996 | Eldon | A47G 9/0215 | |
| | | | 219/211 | |
| 5,711,328 A | 1/1998 | Braun | | |
| 6,002,110 A * | 12/1999 | Sikka | B29C 65/14 | |
| | | | 219/390 | |
| 6,236,020 B1 * | 5/2001 | Friedman | A61C 19/00 | |
| | | | 219/385 | |
| 6,252,202 B1 * | 6/2001 | Zychek | F27B 17/025 | |
| | | | 219/385 | |
| 6,384,381 B2 * | 5/2002 | Witt | A47J 37/0623 | |
| | | | 219/409 | |
| 6,441,354 B1 * | 8/2002 | Seghatol | A61O 5/00 | |
| | | | 219/679 | |
| 6,809,302 B1 * | 10/2004 | Jones | A47J 36/2438 | |
| | | | 219/521 | |
| 6,870,137 B1 * | 3/2005 | Clapp | A45C 11/00 | |
| | | | 219/430 | |
| 7,002,107 B2 * | 2/2006 | Nooh | F24C 7/00 | |
| | | | 219/391 | |
| 7,156,637 B1 * | 1/2007 | Kutsch | A61C 13/206 | |
| | | | 264/17 | |
| 7,570,875 B1 * | 8/2009 | Groves | F26B 3/283 | |
| | | | 219/405 | |
| 7,853,128 B2 * | 12/2010 | Cavada | A47J 37/0807 | |
| | | | 392/416 | |
| 8,487,220 B2 * | 7/2013 | Serrago | F27B 17/025 | |
| | | | 219/390 | |
| 8,921,743 B2 * | 12/2014 | Ewell, Jr. | A47J 27/62 | |
| | | | 219/412 | |
| 9,241,596 B2 * | 1/2016 | Bauer | A47J 36/2433 | |
| 2003/0111751 A1 * | 6/2003 | Monticelli | A61C 13/20 | |
| | | | 264/16 | |
| 2008/0037965 A1 * | 2/2008 | De Luca | H05B 3/0076 | |
| | | | 392/416 | |
| 2008/0093357 A1 * | 4/2008 | Norman | B65D 81/34 | |
| | | | 219/521 | |
| 2009/0265953 A1 * | 10/2009 | Bae | D06F 58/203 | |
| | | | 34/467 | |
| 2012/0175801 A1 * | 7/2012 | Jahns | A61C 13/0003 | |
| | | | 264/19 | |
| 2013/0029279 A1 * | 1/2013 | Jussel | F27B 17/025 | |
| | | | 432/23 | |
| 2013/0158694 A1 * | 6/2013 | Rubbert | A61C 8/0018 | |
| | | | 700/98 | |
| 2013/0230821 A1 * | 9/2013 | Brown | A61O 5/045 | |
| | | | 433/29 | |

\* cited by examiner

HEATING APPARATUS FOR MATERIALS USED IN DENTAL TREATMENT

This application is the U.S. national phase of International Application No. PCT/EP2012/066865 filed 30 Aug. 2012 which designated the U.S. and claims priority to NL 2007327 filed 1 Sep. 2011, the entire contents of each of which are hereby incorporated by reference.

FIELD OF THE INVENTION

This invention relates to a heating apparatus for heating materials used in dental treatment. The heating apparatus comprises a heating compartment with a heating element for heating air inside the heating compartment and at least one socket for receiving and holding at least a part of the materials used in dental treatment inside the heating compartment.

BACKGROUND OF THE INVENTION

In root canal treatment, a patient's root canal is first emptied and cleaned and then filled with an obturator. The obturator is often made of gutta-percha. Gutta-percha is a thermoplastic natural non-elastic latex. Before pressing the thermoplastic obturator into the emptied and cleaned root canal, it is heated to a suitable temperature for softening the obturator material. For this purpose, dedicated heating apparatuses are on the market. Other materials used in the dental treatment are also heated before being used in the dental treatment, such as, for example, composite for filling a tooth, or a liquid which is used for rinsing a tooth, or rinsing a root canal.

An example of such a heating apparatus is the Thermaprep Plus Oven made by Dentsply. This oven comprises a heating chamber for heating thermoplastic obturators placed therein. Before using the obturator for filling a root canal, it is placed in an obturator holder and let down into the heating chamber. The heating time for the thermoplastic obturator varies from 25 to 45 seconds, depending on the obturator size and the used thermoplastic material. When at the right temperature, the obturator can be removed from the holder and placed inside the patient's root canal.

One of the disadvantages of this known heating apparatus is that the dentist has to wait quite a long time before the obturator is at the right temperature for being inserted into the root canal. This problem is only partly solved by providing a second obturator holder and a corresponding second heating chamber. When a first thermoplastic obturator is inside the first heating chamber, the dentist may already place a second obturator in the second obturator holder. By alternately using the two heating chambers, the efficiency of the whole heating process is slightly improved. However, it still takes between 20 and 45 seconds to bring the thermoplastic material to the desired temperature.

OBJECT OF THE INVENTION

It is an object of the invention to provide a heating apparatus that is more efficient in use. Most importantly, a heating apparatus is desired which is able to decrease the amount of time needed for bringing the obturator to the desired temperature.

SUMMARY OF THE INVENTION

According to a first aspect of the invention, this object is achieved by providing a heating apparatus for heating materials used in dental treatment. The heating apparatus comprises a heating compartment with a heating element for heating air inside the heating compartment, at least one socket for receiving and holding at least a part of the materials used in dental treatment inside the heating compartment, and an airflow generator for generating an airflow in the heating compartment.

The flow of hot air inside the heating compartment greatly reduces the amount of time needed for bringing the materials used in dental treatment to the desired temperature. With the heating apparatus according to the invention, the heating of the materials may take less than 5 seconds. Additionally, the air flow results in a more uniform temperature distribution inside the heating compartment. The more uniform temperature distribution improves the possibility to control the exact temperature of the materials. Examples of materials used in dental treatment are filling composite for filling a tooth, an ampoule with a dental rinsing liquid, or, for example, a thermoplastic obturator used for filling a dental root canal.

In a preferred embodiment, the airflow generator is a fan, coupled to a motor for driving the fan, for providing a vortex within the heating compartment. Experiments and simulations have shown that a hot air vortex with a speed of, e.g., 5 m/s, may increase the heat transfer factor with a factor 10.

In an embodiment, the fan is arranged in the heating compartment such that it can rotate around a rotation axis. The fan comprises at least two blades which extend in a radial direction away from the rotation axis. In a further embodiment, at least a portion of the blades are shaped such that an imaginary line following a surface of the blades forms an angle with the rotation axis to create, within the vortex, an airflow in a direction of the rotation axis. If the blades do not form an angle with the rotation axis, the fan only creates a vortex which rotates around the rotation axis. This may result in temperature differences within the vortex. If at least a part of the blades of the fan are tilted with respect to the rotation axis, the blades also move air of the heating chamber in an upwards and/or downwards direction. Thus, within the vortex, air starts also to circulate in a first and second direction, being opposite directions, and the first and second direction are substantially parallel to the rotation axis. Consequently, temperature differences within the vortex are reduced. In an optional embodiment, the angle between the imaginary line and the rotation axis is in between 5 and 85 degrees. In another embodiment, the angle is in between 5 and 45 degrees. In a further embodiment, the angle is in between 10 and 40 degrees.

For further improving the temperature control, one or more temperature sensors may be provided in the heating compartment. When coupling the temperature sensor(s) to the heating element, a temperature control loop can be established.

In a preferred embodiment, the heating apparatus further comprises a rechargeable battery unit for powering the heating element and the motor, the heating apparatus being adapted to be placed on a separate charger for charging the rechargeable battery unit. An important advantage of this embodiment is that the heating apparatus can be used close to the patient, without needing a nearby wall outlet or an extension cord. Only the charger needs to be connected to a wall outlet. The rechargeable battery unit is charged when placed on the charger. When the heating apparatus is needed, it is taken from the charger and placed close to the patient. The heated materials, such as obturators, are taken from the heating apparatus and directly used for the dental treatment, such as the insertion of the obturator into the appropriate root canal. The risks of an obturator cooling too much before insertion and of falling on the floor during the transport from the heating apparatus to the patient are reduced.

After inserting the obturator into the root canal, the obturator handle still extends from the tooth. This obturator handle may be cut off using pliers or the dentist's drill. However, the obturator handle is preferably burned away by a heated tool tip of a dedicated cutting device. In a further embodiment of the heating device according to the invention, also a cutting device is provided. The cutting device comprises a cutting tip for burning the obturator handle from the obturator. The heating device further comprises an electric tool heater circuit and a slot for holding the cutting device in such a way that, when the cutting device is provided in the slot, an electrical contact on the cutting device is connected to the electric tool heating circuit for heating a cutting tip of the cutting device. The electric tool heater circuit is preferably also powered by the rechargeable battery unit described above.

These and other aspects of the invention are apparent from and will be elucidated with reference to the embodiments described hereinafter.

DETAILED DESCRIPTION OF THE INVENTION

Figure 1:
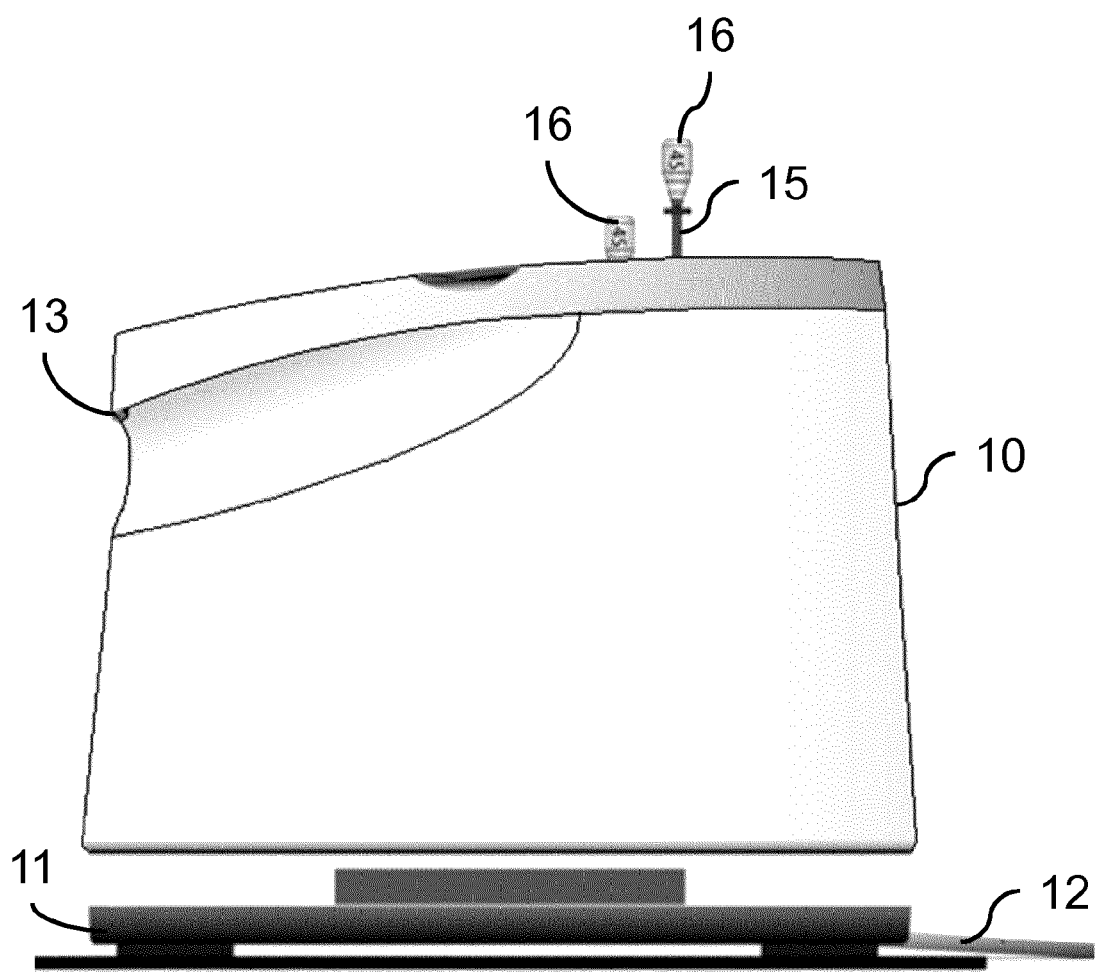
FIG. 1 shows a side view of a heating device according to the invention.

FIG. 1 shows a side view of a heating device 10 according to the invention. The heating device 10 is capable of heating thermoplastic obturators 15 to be used for filling root canals. When a user, probably a dentist, wants to heat an obturator 15, he takes the obturator handle 16 of the obturator 15 between his fingers and hangs the obturator in a socket provided for holding the obturator 15 (see also FIGS. 2 and 3). The thermoplastic obturator material is then heated to the correct temperature. A temperature control knob 13 may be provided for controlling the temperature inside the heating compartment of the heating device 10. It is to be noted that the embodiments of the invention are not limited to heating obturators only. In other embodiment, the heating device 110 is also suitable for heating other material for use in dental treatment, such as filling composite for filling a tooth and a small ampoule with a rinsing liquid.

In this embodiment, the heating device 10 is powered by an internal battery pack, but it may also be powered by a 220V/110V wall outlet. The internal battery pack is preferably rechargeable. A charger 11 is provided for recharging the battery pack when the heating device 10 is placed on it. The charging of the battery pack may be realized via direct electrical connections or via inductive charging. The charger 11 is connected to a wall outlet via a power cord 12. The main advantage of using a charger 11 and a separate heating device 10 is that the wireless heating device 10 can be placed close to the patient when the obturators 15 are needed. The heated obturators 15 do not have to be transported over large distances before being inserted into a root canal. The risk of heated obturators 15 falling on the floor or cooling too much before being used is thereby reduced. No power cords hinder the freedom of movement of the heating device 10 or of people moving through the area close to the heating device 10. The charger 11 can be placed close to a wall outlet. When the heating device 10 is not in use, it is placed on the charger 11 and the battery pack is recharged.

Figure 2:
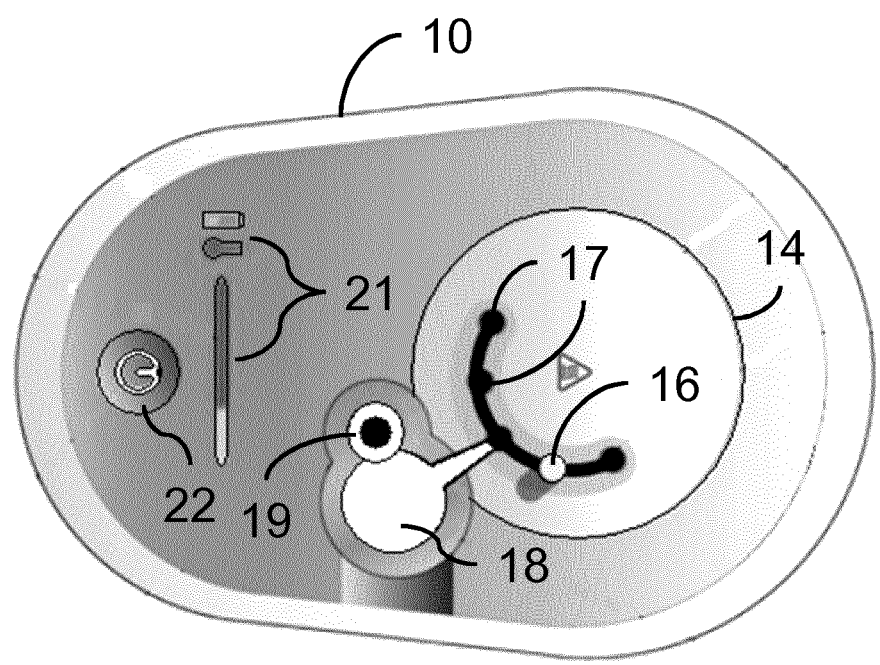
FIG. 2 shows a top view of the heating device of FIG. 1.

FIG. 2 shows a top view of the heating device 10 of FIG. 1. In this view, you can see the obturator handle 16 of an obturator 15 hanging in one of the five obturator sockets 17. The heating device 10 may have any number of obturator sockets 17, but it is practical to provide at least two or three obturator sockets 17 to make it possible to heat multiple obturators 15 simultaneously. Often, more than one obturator 15 is needed for treating one patient. The obturator sockets 17 may be provided in an exchangeable obturator interface 14. When the obturator interface 14 is exchangeable, it is possible to provide different obturator interfaces 14 for different types of obturators, which may have different dimensions. In a preferred embodiment, the obturator interface 14 is recognized by the heating device 10, e.g. mechanically or electronically, and one or more obturator specific device settings are controlled automatically.

Figure 3:
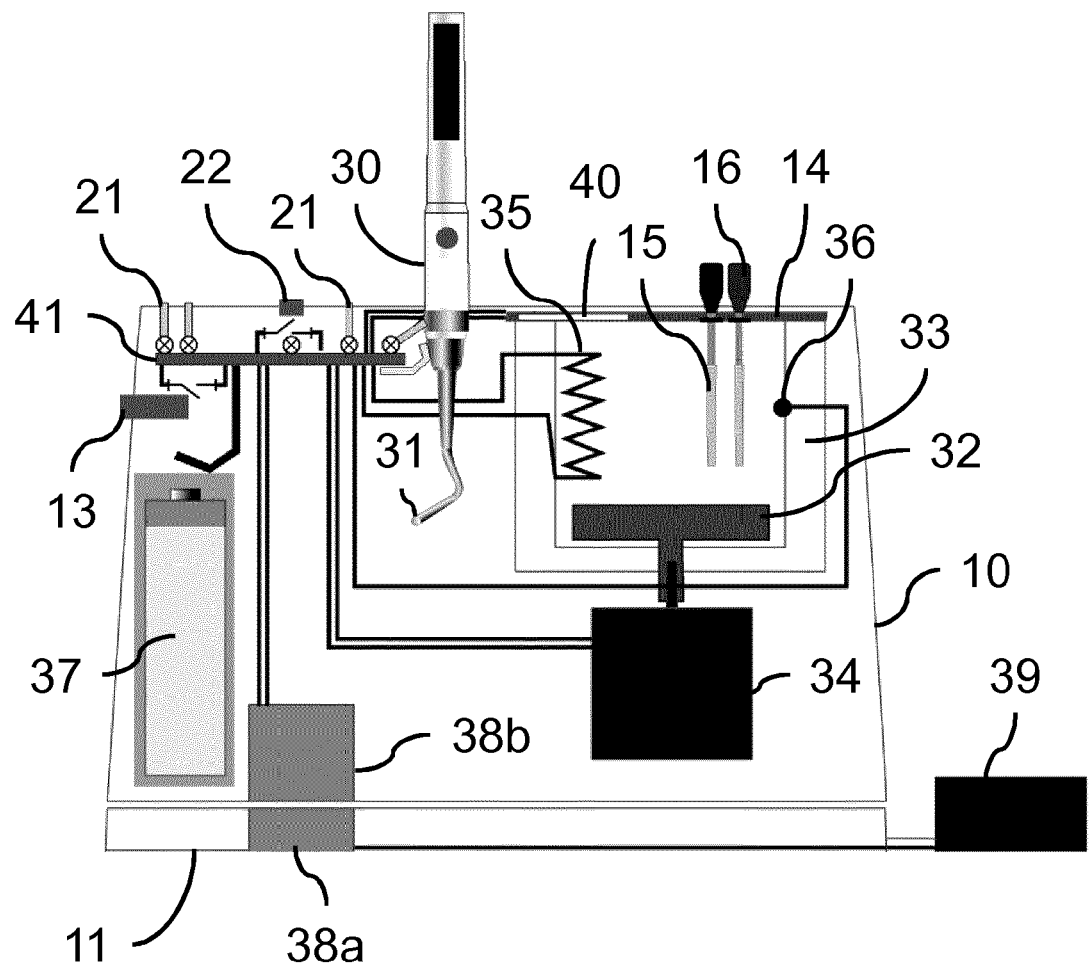
FIG. 3 schematically shows a cross section of the heating device of FIG. 1.

When the obturator interface 14 is removable, it is also easier to clean the heating compartment (see FIG. 3). Cleaning of the heating compartment may be needed when, e.g., obturator parts fall through the obturator sockets 17 into the heating compartment. Cleaning may even be easier when larger parts of the top surface are removable. If the heating device 10 is used to heat other materials used in dental treatment, the obturator interface 14 may have a slightly different shape such that the other materials may be well supported and may be easily inserted into a heating compartment of the heating device 10. In a further embodiment, the obturator interface 14 may have differently shaped sockets 17 which are arranged to receive different materials to be used in the dental treatment, such that the different materials may be heated simultaneously.

The obturator 15 may be inserted into the obturator socket 17 directly from or via a larger opening 18 and a tapered canal leading towards the obturator socket 17. Next to this larger opening 18, a slot 19 for holding and, optionally, heating a cutting device is provided. The use of the cutting device is further elucidated below, with reference to FIG. 4. A heater ready indicator may be provided for indicating when the device 10 is ready for heating the cutting device.

Various indicators 21 may be provided, e.g., for indicating a power level of the battery, a temperature inside the heating compartment or how long an obturator has to be kept in the device until it is ready for use. A power button 22 may be provided for turning the device on or off. The power button 22 may light up, when the heating device 10 is connected to the charger 11.

FIG. 3 schematically shows a cross section of the heating device 10 of FIGS. 1 and 2. In addition to the features already described above, this view shows the heating compartment 33, a fan 32, a temperature sensor 36, a cutting device 30, the rechargeable battery pack 37, a charger connector 38a, 38b, a power adapter 39 and some other features that will be discussed below.

The heating element 35 produces heat for warming the air inside the heating compartment 33. The walls of the heating compartment 33 are preferably air-tight and made of a heat insulating material to make it easier to control the temperature inside the heating compartment 33 and to save energy. According to the invention, a fan 32 is provided for providing a vortex inside the heating compartment 33. The vortex of heated air inside the heating compartment 33 greatly reduces the amount of time needed for bringing the thermoplastic material of the obturator 15 to the desired temperature. As a result, the heating of the obturator material may take less than 5 seconds. Experiments and simulations have shown that a hot air vortex with a speed of, e.g., 5 m/s, may increase the heat transfer factor with a factor ten. Higher vortex speeds may lead to even better results. Additionally, the vortex results in a more uniform temperature distribution inside the heating compartment 33. The more uniform temperature distribution improves the possibility to control the exact temperature of the obturator material. A temperature sensor 36 may be placed in the heating compartment 33 for improving the temperature control. The temperature sensor 36 may be coupled to the heating element and/or the motor 34 of the fan 32 via electronic circuitry for establishing a control loop and keeping the air inside the heating compartment 33 stable and within the preferred temperature range.

The fan 32 is driven by a motor 34 which is powered by the rechargeable battery 37. The rechargeable battery 37 is charged when the heating device 10 is placed on the charger 11 and the charge connectors 38a, 38b couple the battery 37 to a power outlet, optionally via a power adapter 39. The charge connectors 38a, 38b may make an electrical connection or power may be transferred from the charger 11 to the heating device 10 inductively. It is to be noted that, instead of a fan 32 drive by a motor 34, other known ways of producing airflows may be used.

An electronic circuit board 41 is provided for comprising the electronic circuits that control the operation of the device 10. Most or all electronic parts described above are powered by the battery 37 via the electronic circuit board 41. The exchangeable obturator interface 14 comprises a chip 40 for identifying the type of obturators 15 that are going to be used. Depending on the type of obturators 15 to be expected, some of the operational parameters, such as the temperature inside the heat compartment 33 or the rotational speed of the fan 32, may be automatically adjusted.

Figure 4:
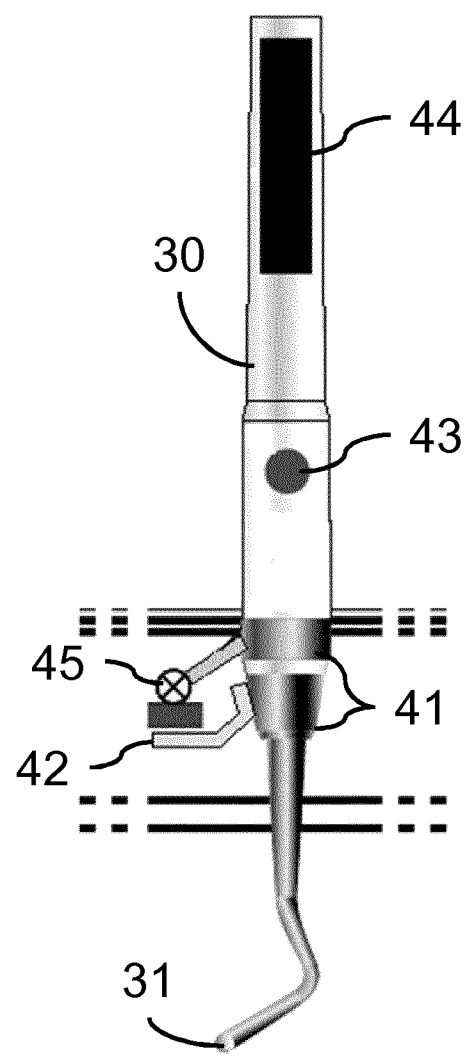
FIG. 4 shows a close up of the cutting device, placed in a dedicated slot of the heating device.

A cutting device 30 for cutting the obturator handles 16 from the obturators 15 after insertion of the obturator into the patient's root canal is provided in a slot 19 provided for this purpose. FIG. 4 shows a close up of the cutting device 30 and the dedicated slot 19. The cutting device 30 comprises a heating tip 31 for burning the obturator handle 16 from the inserted obturator 15. A button 43 is provided for switching on and off an internal heating element of the cutting device 30. When inserted in the corresponding slot 19 of the heating device 10, electrical contacts 41 on the surface of the cutting device 30 close circuit a heating circuit 42 of the heating device 10. A heater ready indicator 45 may be provided in the heating device 10 to indicate when the heating tip 31 is warm enough to be used for cutting off an obturator handle 16. A condensator or rechargeable battery 44 may be provided in the cutting device 30 for keeping the heating tip 31 at the right temperature, when the electrical contacts 41 are not in contact with the heating circuit 42.

Figure 5:
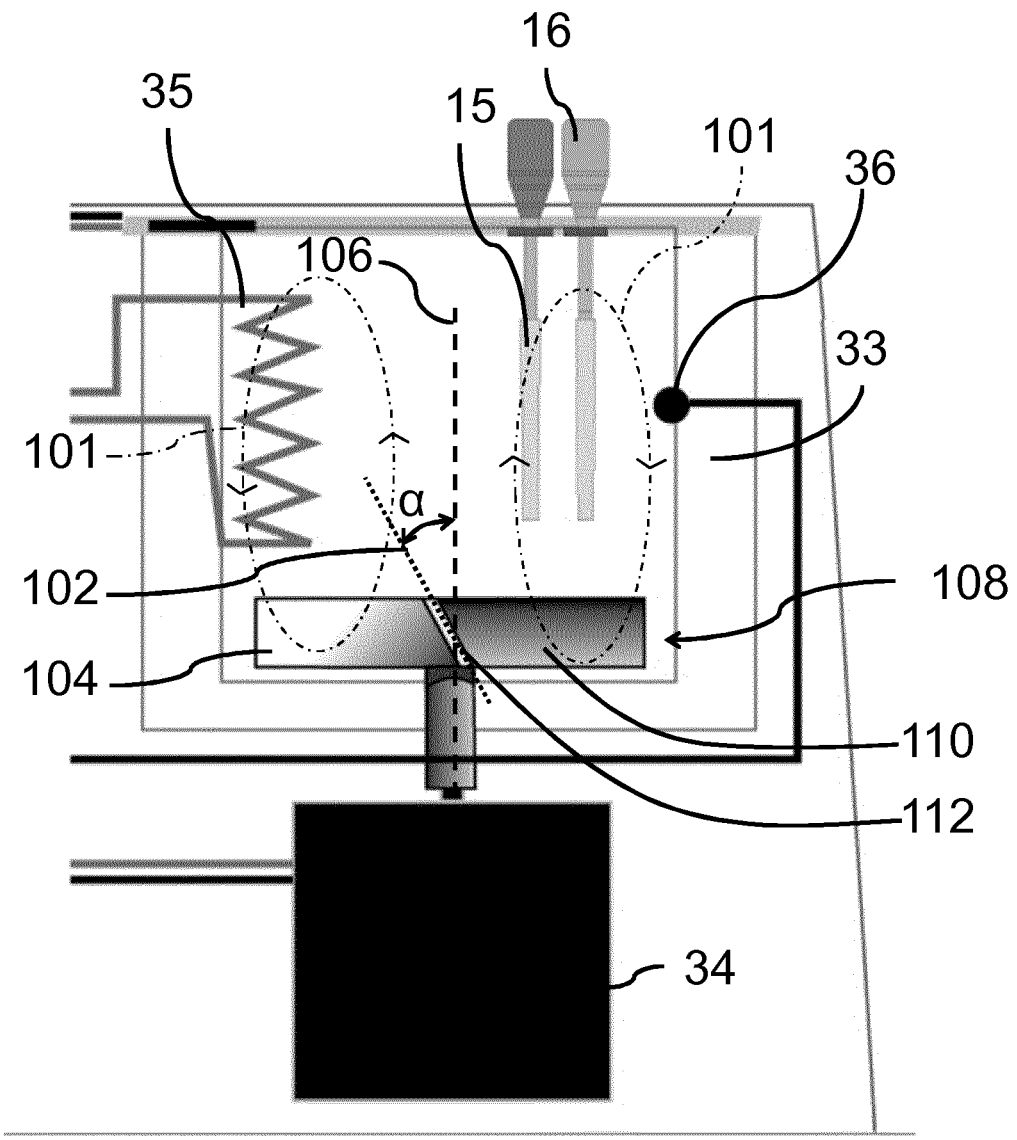
FIG. 5 shows a close up of the heating compartment.

FIG. 5 shows a close up of the heating compartment. As discussed above, the heating compartment 33 comprises a heating element 35, a temperature sensor 36, a fan 32, and may comprise, in use, the obturator(s) 15 which are attached to the obturator handle 16. At a bottom of the heating compartment 33 is provided a fan 108 which rotates, in use, around rotation axis 106. The fan 108 is mechanically connected to the motor 34 which drives, in use, the fan 108. The fan 108 comprises at least two blades. In FIG. 5 three blades 104, 110, 112 are shown. A side surface of blade 112 is shown, which means that blade 112 extends, in the presented position of the fan 108, from the rotation axis 106 in a direction perpendicular to a plane of the drawing of FIG. 5. It is seen that blade 112 is tilted with respect to the rotation axis 106. This means that, when an imaginary line 102 follows a surface of the blade 112, the imaginary line forms an angle α with the rotation axis 106. In FIG. 5 the whole blade 112 is tilted and, in other embodiments, only a portion of the blade 112 is tilted. The other blades 104, 110 are also tilted in a similar way. The result of the tilted blades 104, 110, 112 is that the air flow in the heating compartment does not only follow the direction of the vortex (which is a direction around the rotation axis 106), but that the air also flows in a direction parallel to the rotation axis 106. In FIG. 5 air flows 101 are drawn which are created by the fan 108. The exact direction of air flows 101 depends on the direction in which the fan 108 rotates. At least it may be expected that in a portion of the heating compartment 33 the air flows in an upwards direction (which means: following the rotation axis in a first direction), and that in another portion of the heating compartment 33 the air flows in a downwards direction (which means: following the rotation axis in a second direction which is opposite the first direction). Because of the air flows 101 in a direction following the rotation axis 106, the temperature within the heating compartment 33 is more homogeneously distributed. In an optional embodiment, the angle α between the imaginary line and the rotation axis is in between 5 and 85 degrees. In another embodiment, the angle α is in between 5 and 45 degrees. In a further embodiment, the angle α is in between 10 and 40 degrees. By selecting a specific angle α, in combination with a specific rotational speed, a speed of the air flows 101 may be influenced.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A heating apparatus for heating a thermoplastic obturator, the heating apparatus comprising:
   a heating compartment with a heating element for heating air inside the heating compartment,
   an exchangeable obturator interface comprising at least one obturator socket for receiving and hanging an obturator handle of a thermoplastic obturator so as to hold the thermoplastic obturator inside the heating compartment, and
   an airflow generator for generating an airflow in the heating compartment, wherein
   the heating apparatus is arranged to mechanically or electronically recognize the obturator interface and to automatically control one or more obturator-specific device settings depending on the obturator interface recognized.

2. A heating apparatus according to claim 1, wherein the airflow generator comprises a fan, and a motor coupled to the fan for driving the fan to thereby provide a vortex within the heating compartment.

3. A heating apparatus according to claim 2, wherein the motor, the fan and the heating compartment are arranged such that the vortex leads to an airflow speed of at least 5 m/s within the heating compartment.

4. A heating apparatus according to claim 2, wherein the fan is arranged rotatable around a rotation axis within the heating compartment, and the fan comprising at least two blades extending in a radial direction away from the rotation axis.

5. A heating apparatus according to claim 4, wherein at least a portion of the blades are shaped such that an imaginary line following a surface of the blades forms an angle ($\alpha$) with the rotation axis for creating in at least a portion of the vortex an airflow in a direction parallel to the rotation axis.

6. A heating apparatus according to claim 5, wherein the angle ($\alpha$) is in the range from 5 degrees to 85 degrees.

7. A heating apparatus according to claim 1, further comprising a rechargeable battery unit for powering the heating element and the airflow generator, the heating apparatus being adapted to be placed on a separate charger for charging the rechargeable battery unit.

8. A heating apparatus according to claim 2, further comprising a rechargeable battery unit for powering the heating element and the motor of the airflow generator.

9. A heating apparatus according to claim 2, further comprising an electric tool heater circuit and a slot for holding a cutting device in such a way that, when the cutting device is provided in the slot, an electrical contact on the cutting device is connected to the electric tool heating circuit for heating a cutting tip of the cutting device.

10. A heating apparatus according to claim 1, further comprising a heat sensor for measuring a temperature inside the heating compartment, the heat sensor being part of a control loop for controlling the temperature inside the heating compartment.

11. A heating apparatus according to claim 1, wherein the exchangeable obturator interface comprises a chip for identifying the obturator interface and automatically adjusting at least one specific device setting depending on the obturator interface identified thereby.

12. A heating apparatus according to claim 2, wherein the airflow generator comprises a fan, and a motor coupled to the fan for driving the fan to thereby provide a vortex within the heating compartment.

13. A heating apparatus according to claim 12, wherein the exchangeable obturator interface comprises a chip for identifying the obturator interface, and wherein the specific device setting which is automatically adjusted depending on the obturator interface identified by the chip is at least one selected from the group consisting of a temperature inside the heat compartment and a rotational speed of the fan.

\* \* \* \* \*